(12) United States Patent
Matsutani et al.

(10) Patent No.: US 6,554,840 B2
(45) Date of Patent: Apr. 29, 2003

(54) MEDICAL SCALPEL (75) Inventors: Kanji Matsutani, Tochigi-ken (JP); Masahiko Saito, Tochigi-ken (JP)

(73) Assignee: Mani, Inc., Tochigi-ken (JP)

( * ) Notice: Subject to any disclaimer, the term of this patent is extended or adjusted under 35 U.S.C. 154(b) by 0 days.

(21) Appl. No.: 09/794,493

(22) Filed: Feb. 28, 2001

(65) Prior Publication Data
US 2001/0029386 A1 Oct. 11, 2001

(30) Foreign Application Priority Data
Feb. 29, 2000 (JP) ........................................ 2000-052702

(51) Int. Cl.[7] ............................................... A61B 17/32
(52) U.S. Cl. ........................ 606/107; 606/167; 606/166
(58) Field of Search ................................ 606/107, 159, 606/118, 183, 185, 131, 135, 137, 161, 166, 167, 170, 4, 6, 5; 30/348, 346, 346.55; D11/90; D24/146, 147

(56) References Cited

U.S. PATENT DOCUMENTS

| | | | | |
|---|---|---|---|---|
| 5,201,747 A | * | 4/1993 | Mastel | 606/167 |
| 5,217,476 A | * | 6/1993 | Wishinsky | 606/167 |
| 5,222,967 A | * | 6/1993 | Casebeer et al. | 606/166 |
| 5,405,355 A | * | 4/1995 | Peyman et al. | 606/166 |
| 5,713,915 A | * | 2/1998 | Van Heugten et al. | 606/167 |
| D405,178 S | * | 2/1999 | Dykes | 606/166 |
| 6,056,764 A | * | 5/2000 | Smith | 606/167 |
| 6,099,543 A | * | 8/2000 | Smith | 606/167 |
| 6,139,559 A | * | 10/2000 | Nordan et al. | 606/166 |
| RE37,304 E | * | 7/2001 | Van Heugten et al. | 606/167 |
| 6,264,668 B1 | * | 7/2001 | Prywes | 606/167 |

* cited by examiner

Primary Examiner—Gloria M. Hale
(74) Attorney, Agent, or Firm—Townsend & Banta (57) ABSTRACT The present invention relates to a medical scalpel for incising a spherical biological tissue comprising a shank and a planar blade portion integrated with the shank. The planar blade portion has a first face and a second face opposed in parallel as a whole with each other. The planar blade portion has a pointed end to thereby show a reverse-V profile and has, on both sides of such pointed end, an edge in parallel as a whole with the first face and the second face, the blade portion being formed so as to have a ratio of the partial thickness thereof on one side of a virtual flat plane surrounded by said edge to the total thickness thereof within a range of from 75 to 93%.

6 Claims, 8 Drawing Sheets

MEDICAL SCALPEL

TECHNICAL FIELD

The present invention relates to a medical scalpel for incising spherical biological tissues, and in particular to a medical scalpel capable of producing a highly auto-closable incisional vulnus in eyeball incision.

BACKGROUND ART

In the conventional ophthalmic surgery, incision of cornea or interstice of cornea and sclera inevitably requires successive suture or ligation of incised cornea or sclera. A suture may, however, pressurize the cornea or sclera, which tends to retard recovery of eyesight or to produce postoperative astigmatism. So that recent trends in the surgery relate to production of auto-closable incisional vulnus which automatically closes without needing suture.

Figure 5A:
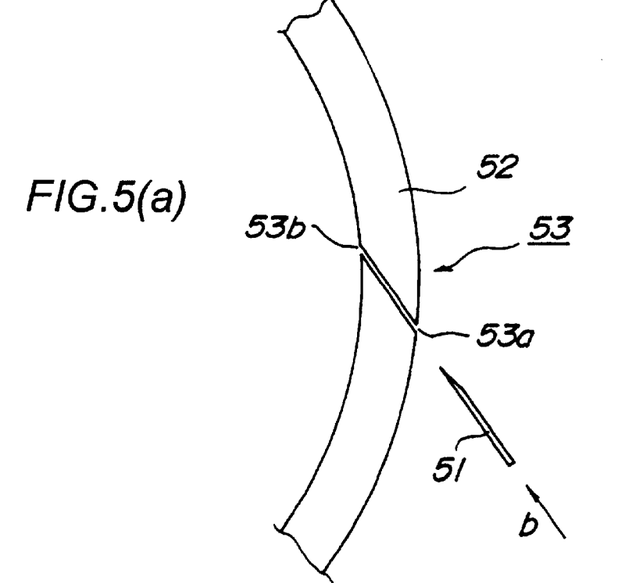
FIGS. 5A and 5B are sectional views explaining an auto-closable incisional vulnus.
Figure 5B:
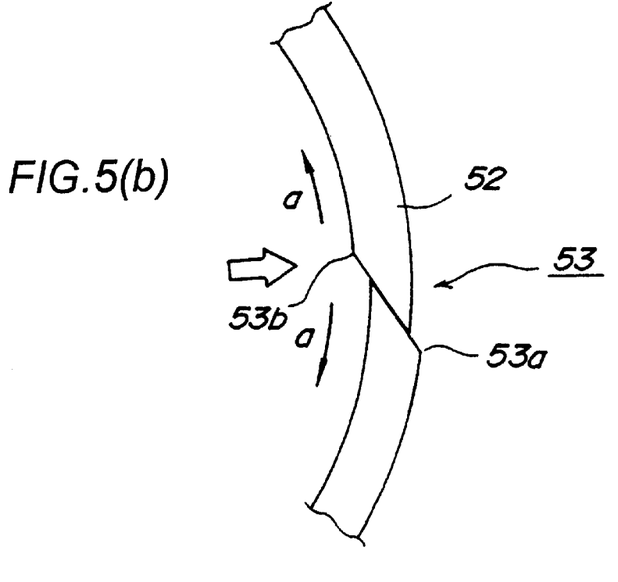

A preferable and highly auto-closable incisional vulnus will be explained referring to FIGS. 5A and 5B, and FIGS. 6A to 6C. As shown in FIG. 5A, when a cornea 52 is incised with a scalpel 51 in a direction oblique to the thickness thereof to produce an incisional vulnus 53 (this is generally done, in a front view of an eyeball, by piercing the scalpel 51 in a direction from lower to obliquely upper), intraocular pressure will be exerted to pressure-open the cornea 52 (in a direction energizing the cornea 52 along an arrow "a"), to thereby close the incisional vulnus 53 by pressure contact.

Figure 6A:
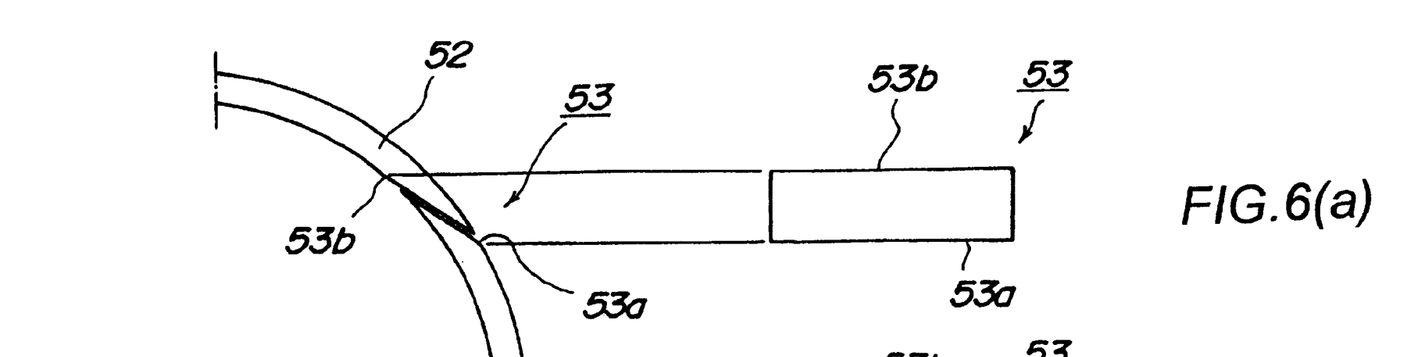
FIGS. 6A to 6C are views of an auto-closable incisional vulnus viewed from the front of the eyeball.
Figure 6B:
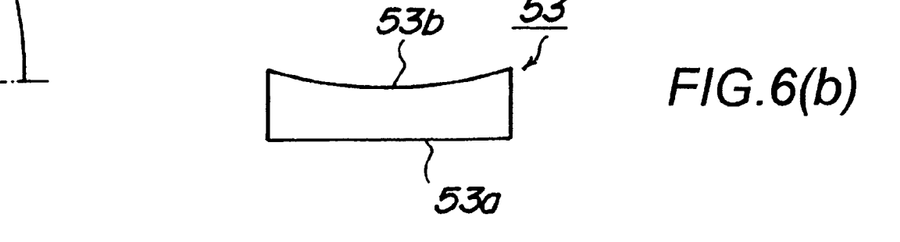
Figure 6C:
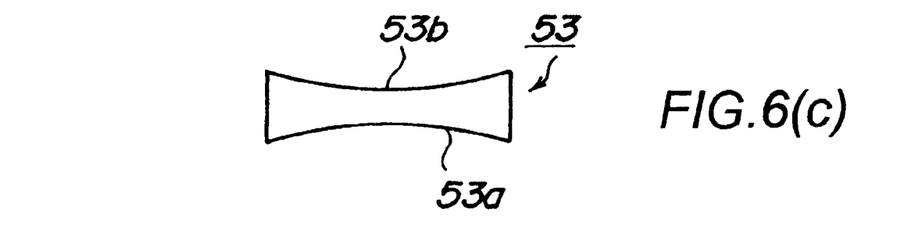

While a morphology of such preferable, highly auto-closable incisional vulnus will differ whether it is viewed from a direction of the scalpel insertion or front of the eyeball since the eyeball has a spherical surface, a front view of the eyeball shows an external incisional line 53a formed on the external of the cornea 52, which is given as a straight line as shown in FIG. 6A, or as curved lines bulging toward an internal incisional line 53b as shown in FIGS. 6B and 6C.

Figure 7A:
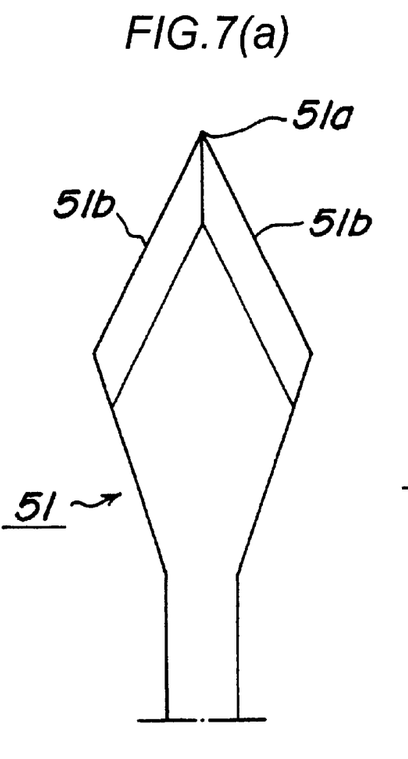
FIGS. 7A and 7B are top views showing conventional scalpels.
Figure 7B:
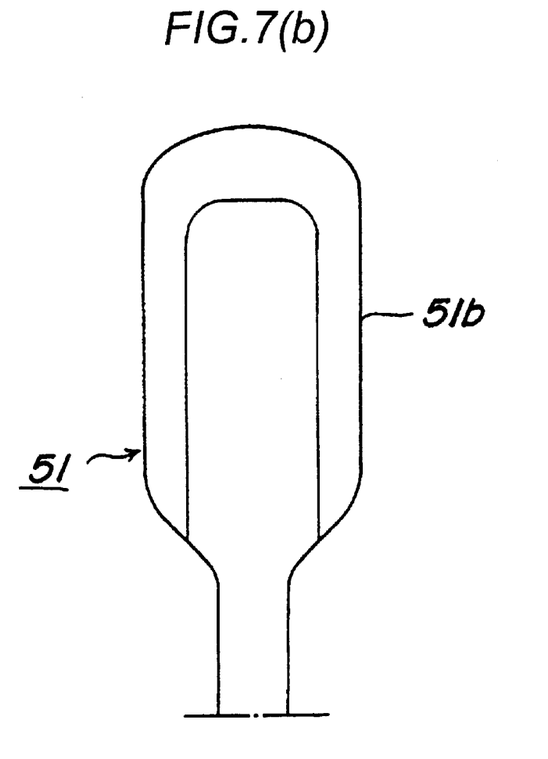
Figure 7C:
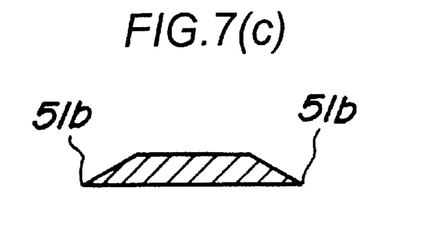
FIGS. 7C and 7D are sectional views respectively showing sections of such scalpels.
Figure 7D:
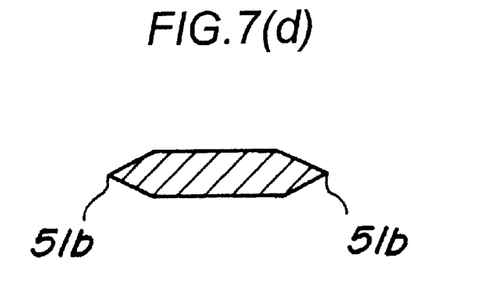

The scalpel 51 used for incising the eyeball will now be described referring to the drawings. The scalpel 51 shown in FIG. 7A has a sharp pointed end 51a and peripheral cutting edges 51b, and that shown in FIG. 7B has a cutting edge 51b rounded along the entire periphery rather than having a pointed end. Sectional forms of such scalpel 51 being generally employed include a trapezoid having a virtual line connecting the cutting edge 51b as a base as shown in FIG. 7C (bevel-up type), and flattened hexagon having a line connecting the cutting edge 51b approximately at the center of the total thickness of the blade portion as shown in FIG. 7D (bi-bevel type).

In eyeball incision, the scalpel 51 is opposed to the cornea 52 so as to allow formation of the auto-closable incisional vulnus 53, and is forwarded straight along a direction indicated by arrow "b" in FIG. 5A. The scalpel 51 is then moved rightward or leftward according to a purpose of the surgery, to widen the incisional vulnus 53.

It is known that such preferable, highly auto-closable incisional vulnus has the external incisional line which gently curves as bulging toward the center of the eyeball or runs straight when viewed from the front of the eyeball. On the contrary, a less auto-closable incisional vulnus is known to have the external incisional line which gently curves as bulging away from the center of the eyeball when viewed from the front of the eyeball, and is likely to turn over when pressure is exerted on the cornea to thereby undesirably incorporate foreign matters or bacteria contained in lacrimal fluid into the eye, so that such vulnus needs suture to enhance auto-closable property. It has, however, been difficult to produce a preferable, highly auto-closable incision vulnus using a generally known scalpel.

Figure 8:
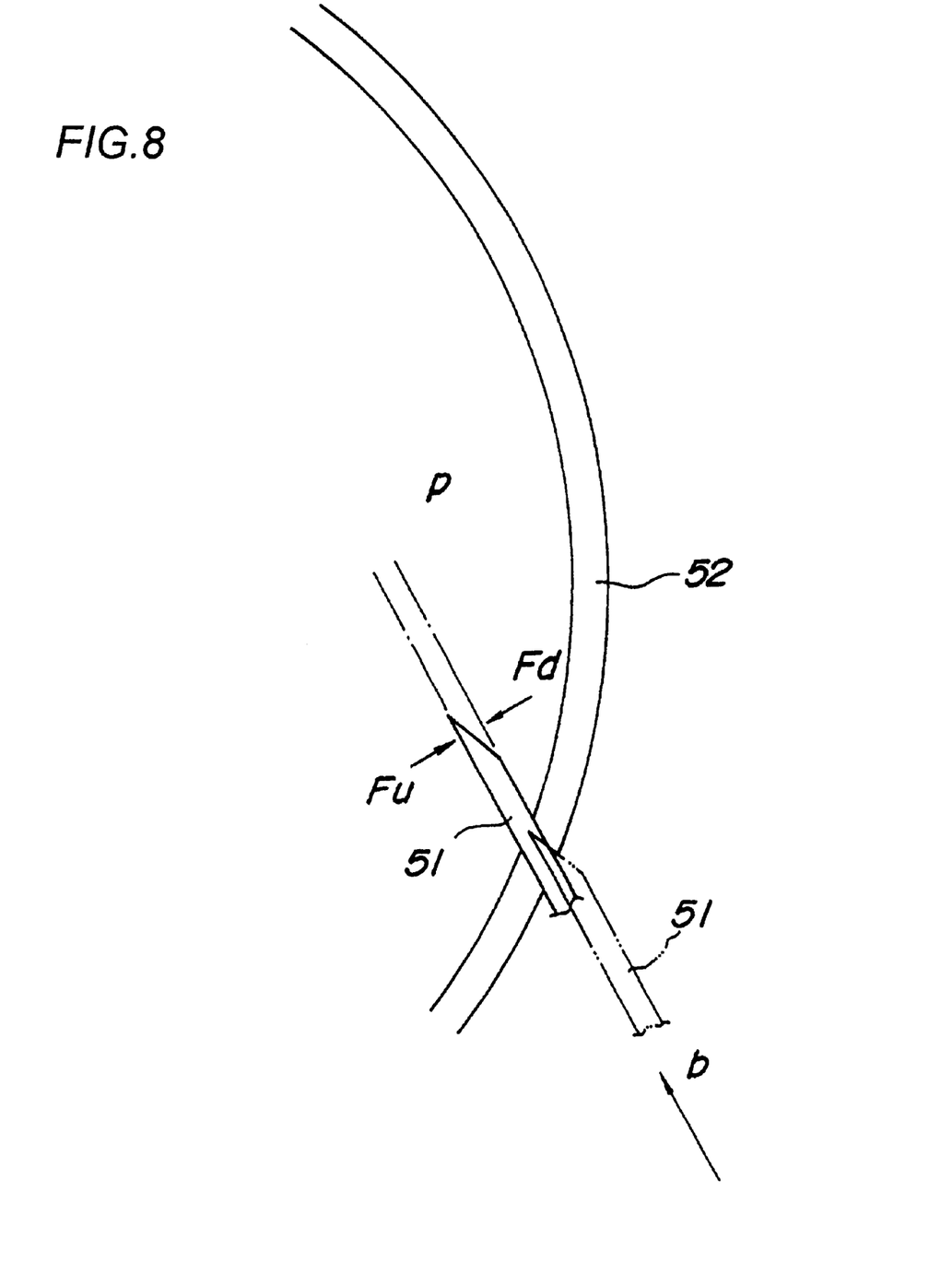
FIG. 8 is a view explaining motion of a scalpel during incision of an eyeball.

More specifically, a bevel-up scalpel 51 shown in FIG. 8 causes on both planes of the blade portion thereof different amounts of force due to pressure p ascribable to the ocular tension and incision resistance when pierced into the cornea 52 (that is, downward force $F_d$ exerted on the upper plane comprising an upper plane and a slant plane is larger than upward force $F_u$ exerted on the base plane), so that the entire portion of the scalpel 51 will shift toward the base plane as it advances deeper into the eye. So that an incisional vulnus thus produced will have a reversed V-form when viewed from the direction of the scalpel insertion, which comprises a tip portion corresponding to the pointed end 51a and straight portions extending from such tip portion toward the ends. Such incisional vulnus will, however, have the tip portion and curves extending from the such tip portion when viewed from the front of the eyeball. Such tip portion is likely to dislocate and may cause astigmatism after the auto-closure.

The bi-bevel scalpel causes on both sides of the blade portion thereof balanced forces ascribable to the ocular tension and incision resistance, so that no vertical force enough for dislocating the scalpel will be generated The incisional vulnus thus produced will have a straight profile as viewed from the direction of the scalpel insertion, but will have an external incisional line bulging away from the center of the eyeball, which makes the incisional vulnus less auto-closable.

It is therefore an object of the present invention to provide a medical scalpel capable of producing a preferable, auto-closable incisional vulnus.

SUMMARY OF THE INVENTION

A medical scalpel of the present invention is such that for incising a spherical biological tissue which comprises a shank, and a planar blade portion being associated to said shank and having a first face and a second face one of which is formed flat at least wherein said blade portion having an edge in parallel as a whole with said flat first face or said second face, and being formed so as to have a ratio of the partial thickness thereof on one side of a virtual flat plane surrounded by said edge to the total thickness thereof which resides within a range from 75 to 93%.

Such medical scalpel (simply referred to as scalpel, hereinafter) has along the outer periphery of the blade portion at least two slopes composing both sides thereof, and the partial thickness of such blade portion on one side (the upper side, for example) of a virtual flat plane surrounded by such edge accounts for 75 to 93% of the total thickness of the blade portion. Such setting allows the force exerted on the upper side of the edge, that is the force pushing the scalpel downward, to become larger than the upward force exerted on the lower side.

Difference between the downward force and upward force is, however, smaller than that in the conventional bevel-up scalpel by virtue of cancellation therebetween, so that a slight downward dislocation of the scalpel will occur when the scalpel is pierced into the eyeball, to thereby produce the external incisional line gently bulging toward the center of the eyeball or extending straightly when viewed from the front of the eyeball. Hence, the external incisional line can have a profile equivalent to that illustrated in FIG. 6C, to thereby produce a preferable, highly auto-closable incisional vulnus.

The force exerted on the blade portion along the direction from the upper face side to the lower face side when the edge is pierced into the eyeball can properly be adjusted by selecting the upper partial thickness within a range from 75 to 93% of the total thickness, which defines the travel distance of such blade portion from the upper face side to the lower face side. Thus the shape of the incisional vulnus can readily be selected depending on such travel distance, to thereby form a desired incisional vulnus with an excellent auto-closable property.

BRIEF DESCRIPTION OF THE DRAWINGS

The above and other objects and features of the invention are apparent to those skilled in the art from the following referred embodiments thereof when considered in conjunction with the accompanied drawing, in which.

DETAILED DESCRIPTION OF THE INVENTION

Preferred embodiments of the scalpel will be explained hereinafter referring to FIGS. 1 to 4B.

Figure 1:
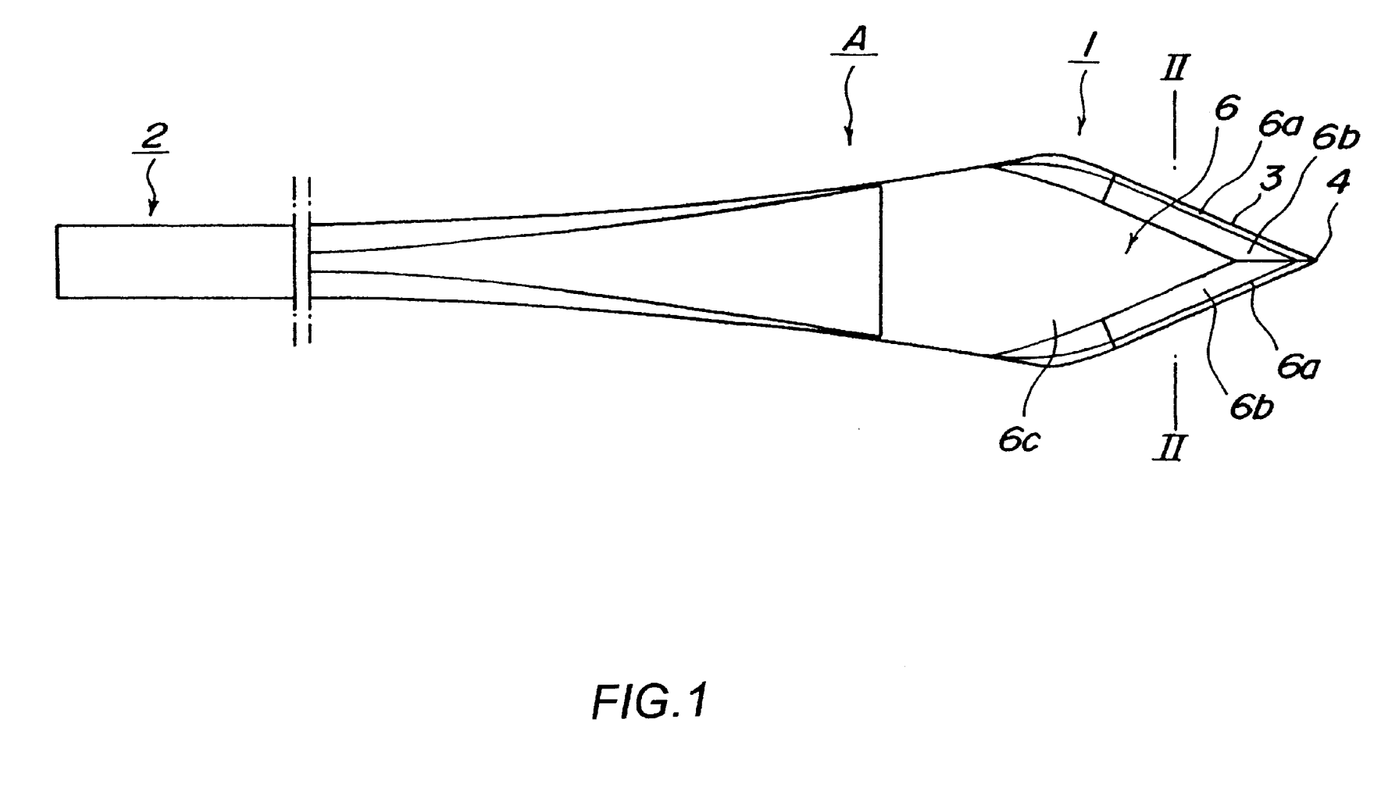
FIG. 1 is a plan view of a scalpel.
Figure 2:
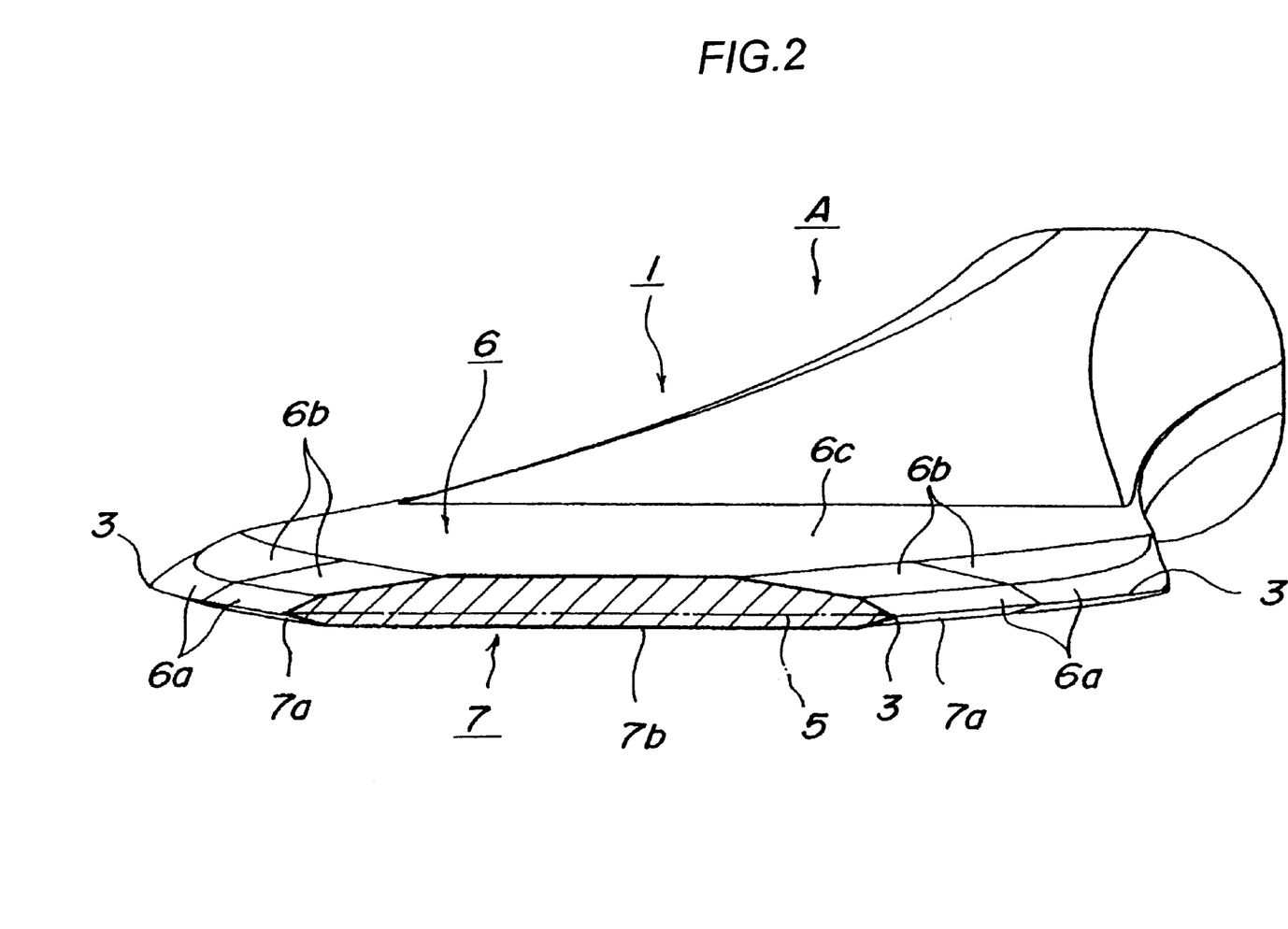
FIG. 2 is a perspective view of the scalpel partially sectioned along line II—II in FIG. 1.
Figure 3:
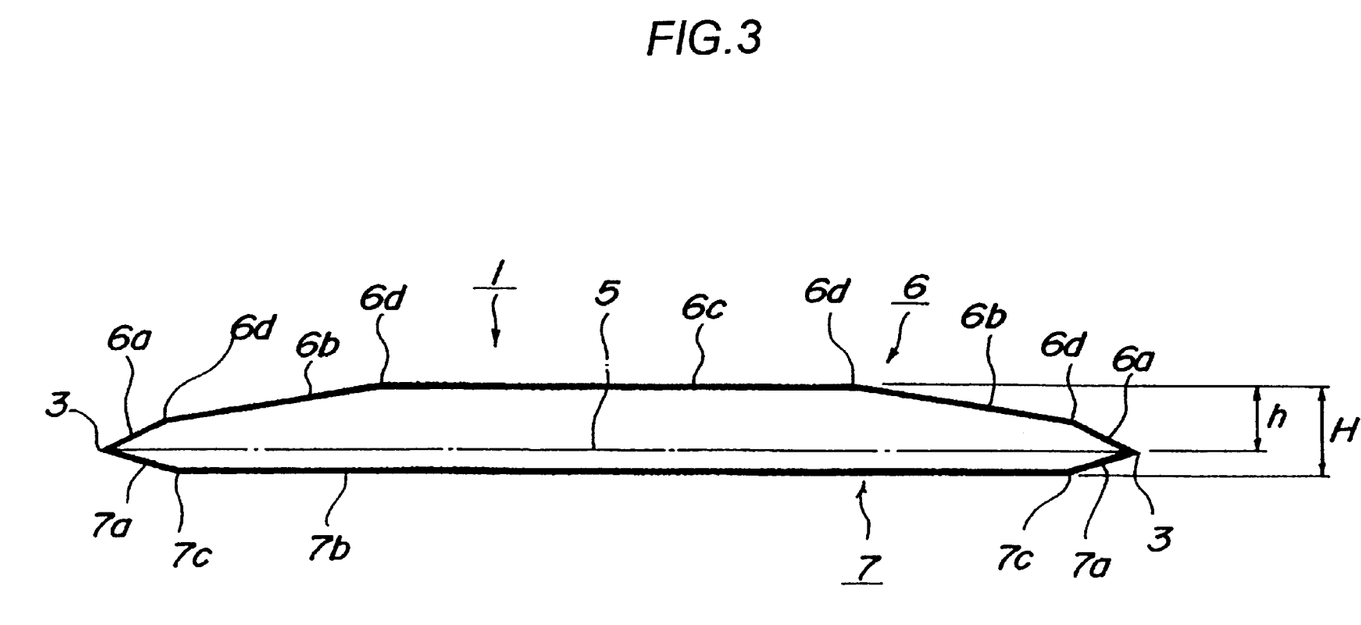
FIG. 3 is a sectional view of the scalpel taken along line II—II in FIG. 1.

In FIG. 1, a scalpel "A" is designed to allow simple production of an auto-closable incisional vulnus to a cornea or sclera in surgery of an eyeball, which is an example of a spherical biological tissue. The scalpel "A" comprises a blade portion 1 having a predetermined plane form and sectional form and a shank 2 extended therefrom. The blade portion 1 has an edge 3 on the outer periphery thereof The blade portion 1 shown in FIG. 1 is formed in a rhombic shape having an acute pointed end 4 to thereby show a reverse-V profile, has the edge 3 on the outer periphery thereof, and further comprises upper end slopes 6a including such edge 3, easy slopes 6b continued from such upper end slopes 6a and having a smaller angle of inclination, and a horizontal plane 6c. FIGS. 2 and 3 shows a section taken along line II—II in FIG. 1, in which the section of the blade portion 1 has on the upper side of a virtual flat plane 5 surrounded by the edge 3 an upper face (a first face) 6 which comprises five planes (the upper end slopes 6a, easy slopes 6b and horizontal plane 6c); and has on the lower side the virtual flat plane 5 a lower face (a second face) 7 which comprises three planes (the lower end slopes 7a and a horizontal plane 7b).

The shank 2 is formed as integrated with the blade portion 1, and has a rod shape having a round section. That is, the blade portion 1 is obtained by processing a rod member by press forming and grinding, so as to have a rhombic plane form and a stereoscopic form in which upper face 6 and the lower face 7 are formed on both sides of the virtual flat plane 5 surrounded by the edges 3 and are abutted at such edges 3.

The edges 3 serve as a cutting edge formed on the outer periphery of the blade portion 1, and is produced by abutting the upper end slope 6a composing the upper face 6 and the lower end slope 7a composing the lower face 7 at an acute angle sufficient for ensuring an excellent cutting performance. Such composed edges 3 well match to surgery to be operated by being pierced into an eyeball and producing an incisional vulnus into a cornea or sclera.

The angle between the upper end slope 6a and the lower end slope 7a was found to be preferable when selected within a range from 12 to 40° in terms of achieving a high durability and cutting performance of the cutting blade, and more preferable when selected within a range from 20 to 36° in consideration of the purpose of the present embodiment relating to eyeball incision, thickness of the scalpel employed, and a ratio of area of the upper and lower end slopes 6a and 7a of the blade portion 1.

The pointed end 4 is formed by abutting the edges 3 at an acute angle, so as to ensure a simple procedure for piercing into the cornea or sclera. It should now be noted that it is not always necessary for the scalpel to have such pointed end 4, and can have a near-straight or round profile at the tip of the blade portion 1 as described later. That is, composing the tip of the blade portion 1 with the pointed end 4 or those with other shapes may be optional according to purposes of the surgery.

The virtual flat plane 5 is a plane surrounded by the edges 3 formed on the outer periphery of the blade portion 1, so that it is not visually recognizable.

The upper face 6 is composed of two upper end slopes 6a including the edges 3, two easy slopes 6b as continued from the slopes 6a, and one horizontal plane 6c connecting such easy slopes 6b. Arrises 6d are formed between the upper end slopes 6a and the easy slopes 6b abutted at an obtuse angle, and between the easy slopes 6b and the horizontal plane 6c abutted similarly. The lower face 7 is composed of two lower end slopes 7a including the edges 3, and one horizontal plane 7b connecting such lower end slopes 7a. Arrises 7c are formed between the lower end slopes 7a and horizontal plane 7b abutted at an obtuse angle.

The upper end slopes 6a and the lower end slopes 7a extend along the edges 3 while keeping constant widths, so as to be provided as band-like planes. The arrises 6d formed between the upper end slopes 6a and the easy slopes 6b abutted with each other are aligned in parallel with the virtual flat plane surrounded by the edge 3.

While the easy slopes 6b are finished by grinding with a relatively coarse grinding stone to thereby have a relatively coarse texture, the upper end slopes 6a and the lower end slopes 7a are finished by grinding with a relatively fine grinding stone to thereby have a relatively fine texture. Because, the upper end slopes 6a is steeper than the easy slope 6b, small space is formed to reduce pressure of biological tissue to the horizontal plane 6c and penetrating resistance is reduced. Also for this construction, product efficiency is promoted.

Assuming now a thickness defined by the upper face 6 and lower face 7 as "H" (a distance between the horizontal planes 6c and 7b, or a total thickness), and a thickness defined by the virtual flat plane 5 and the upper face 6 as "h" (a distance between the virtual flat plane 5 and the horizontal plane 6c, or an Lipper partial thickness), the upper partial thickness "h" is set within a range from 75 to 93% of the total thickness "H". In the present embodiment, the total thickness "H" is approx. 0.14 mm and the upper partial thickness is approx. 0.12 mm, in which the upper partial thickness "h" is equivalent to approx. 86% of the total thickness "H".

Thus composed scalpel "A" can produce upward force and downward force ascribable to the ocular tension and incision resistance applied on the entire portion of the upper and lower surfaces 6, 7 of the blade portion 1, so that the blade portion 1 is affected by difference between these forces. Since the blade portion 1 has a larger thickness on the side of the upper face 6 than on the side of the lower face 7 bounded by the virtual flat plane 5, the blade portion 1 will eventually be applied with downward force along a direction from the upper face 6 to the lower face 7.

Such downward force exerted on the blade portion 1 is, however, small enough as compared with that caused by the conventional bevel-up scalpel. That is, a downward travel distance toward the lower face 7 in the piercing of the blade portion 1 will be smaller than that of the conventional bevel-up scalpel, and such travel distance can properly be adjusted by selecting the upper partial thickness and the lower partial thickness bounded by the virtual flat plane 5 (that is, by selecting the ratio of the upper partial thickness "h" to the total thickness, "H").

Thus adjusting the travel distance toward the lower face 7 in the scalpel insertion can produce in the eyeball a linear incisional vulnus which has a center corresponding to the pointed end 4 and bilaterally runs away from such center gently toward the lower face 7 of the scalpel "A". Such incisional vulnus has an incisional line gently bulging toward the center of the eyeball, or appears as approximately linear as a whole when viewed from the front of the eyeball, so that the vulnus is less likely to turn over and to thereby improve the auto-closable property.

As described in the above, the incisional vulnus can be produced in a desired form and thus ensure an excellent auto-closable property by properly selecting the upper partial thickness and the lower partial thickness bounded by the virtual flat plane 5.

In particular, the ratio of the upper partial thickness "h" to the total thickness "H" less than 75% will approximate the cutting property of the scalpel to that of the conventional bi-bevel scalpel, and the incisional vulnuis will have a curved incisional line bulging away from the center of the eyeball in a front view of the eyeball, so that the vulnus is likely to turn over and thus degrades the auto-closable property.

On the other hand, the ratio of the upper partial thickness "h" to the total thickness "H" exceeding 93% will approximate the cutting property of the scalpel to that of the conventional bevel-up scalpel, and the incisioanl vulnus will have a tip portion corresponding to the pointed end 4 similarly in the case with the bevel-up scalpel, which is undesirable since such tip portion is likely to dislocate.

Experiments by the present inventors revealed that selecting the ratio of the upper partial thickness "h" to the total thickness "H" within a range from 75 to 93% successfully produces in the eyeball a linear and highly auto-closable incisional vulnus which has a center corresponding to the pointed end 4 and bilaterally runs away from such center gently toward the lower face 7 of the scalpel "A", which could simultaneously achieve an excellent durability and cutting a property of the cutting blade. The experiments have also revealed that more improved auto-closable property can be obtained by selecting the ratio of the upper partial thickness "h" to the total thickness "H" within a narrower range from 80 to 90%.

The scalpel "A" should have an excellent cutting property and should not be causative of rusting during marketing or storage. The scalpel "A" is thus made from a wire rod of austenitic stainless steel and is fabricated by cold wire drawing, to thereby attain an excellent hardness based on work hardening and acquire an excellent strength by stretching the metal texture in a fiber form.

The material drawn by the cold wire drawing is cut in a length suitable for fabricating the target scalpel "A", and one end of the cut material is subjected to press forming to produce the blade portion 1 and the other end is processed into the shank 2 having a round rod form. The outer periphery of the blade portion 1 is then ground with a grinding stone or the like, and is further subjected to chemical polishing or electrolytic polishing, to thereby form the edges 3 which can function as a cutting edge.

In particular, in the present embodiment, the total thickness "H" of the blade portion 1 is selected to a value not more than 40% of the diameter of the shank 2, as illustrated in FIG. 2, which ensures an appropriate hardness of the blade portion 1 and a width of the blade portion 1 suitable for producing a desired incisional vulnus.

While the above description dealt with a case using austenitic stainless steel as a material for composing the scalpel, the material is by no means limited thereto, and using a quenchable martensitic stainless steel, for example, can also provide absolutely the same effect if the foregoing shape is employed. That is, there is no specific limitation on materials composing the medical scalpel as long as required characteristics are satisfied.

While the section of the blade portion 1 described in the present embodiment is surrounded by the upper face 6 composed of five planes 6a, 6a, 6b, 6b and 6c; and the lower face 7 composed of three planes 7a, 7a and 7b; the shape of the section is by no means limited thereto.

Figure 4A:
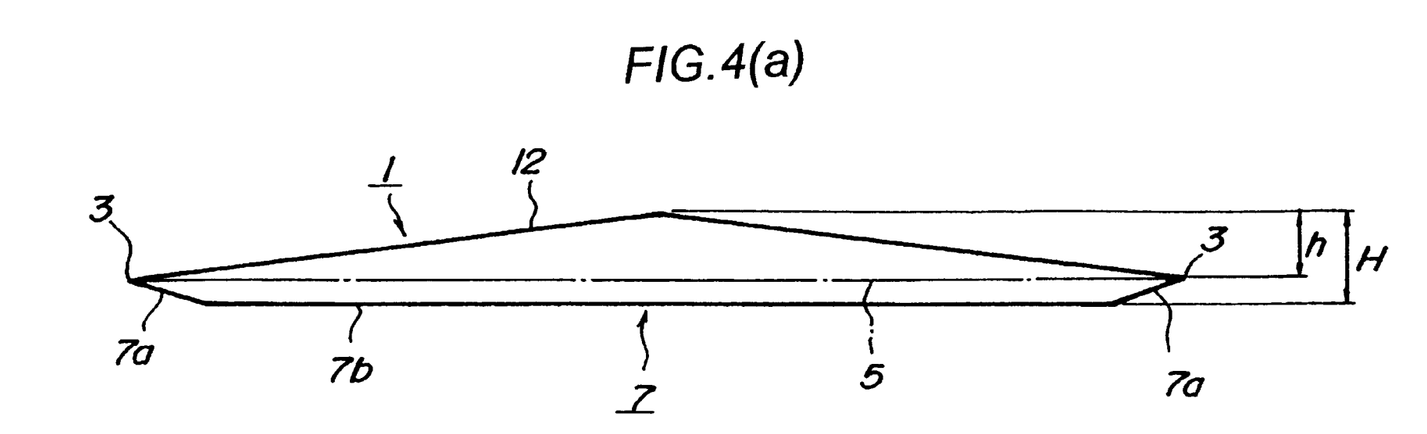
FIGS. 4A and 4B are sectional views showing other examples of the scalpel.
Figure 4B:
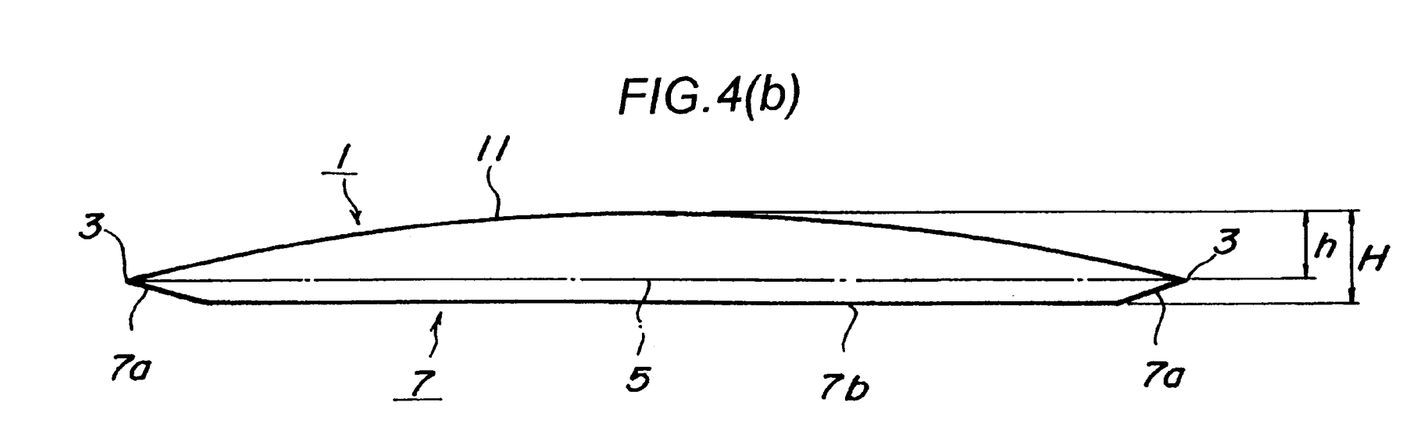

That is, as for the scalpel of the present invention, important is a ratio of the upper partial thickness "h" to the total thickness "H" of the blade portion 1, but not a shape, in terms of ensuring practical cutting performance and durability. So that it is also allowable for the sectional shape of the blade portion 1 to have a triangular upper face 12 comprising two planes over the virtual flat plane 5 as shown in FIG. 4A, of to have a curved upper face 11 over the virtual flat plane 5 as shown in FIG. 4B. The upper face 6 can also be composed of the upper end slopes 6a including the edge 3 and the horizontal plane 6c directly linked to such upper end slopes 6a rather than being interposed with the easy slopes 6b, which of course ensures the same effects. Whatever the sectional shape of the blade portion 1 is, an essential issue is that the ratio of the upper partial thickness "h" to the total thickness "H" resides in a range from 75 to 93%.

While the blade portion 1 described in the present embodiment has a rhombic plane form with the acute pointed end 4, the plane form is by no means limited thereto. For instance, it is also allowable to employ a blade portion having an approximately linear end as shown in FIG. 7B for explaining the conventional example. Using such scalpel also allows incision of the cornea or sclera of the eyeball to thereby produce a highly auto-closable incisional vulnus by virtue of the edge formed on the outer periphery of such blade portion.

In such composed scalpel, the individual planes 6a to 6c composing the upper face 6 and planes 7a and 7b composing the lower face 7 are preferably formed so as to be slightly concaved approximately at the central portions thereof. Slightly concaving the individual planes at the central portions thereof will successfully reduce the contact area with the biological tissues and thus reduce the piercing resistance during the incision of the cornea or sclera, which is beneficial in reducing ophthalmologist's fatigue and patient's pain.

While the foregoing embodiment dealt with the incision of an eyeball as an exemplary spherical biological tissue, the present invention can undoubtedly ensure similar effects when other spherical biological tissues (sac-formed biological tissues, for example) other than eyeball are to be incised.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention should not be limited by the specification, but should be defined by claims set forth below.

What is claimed is:

1. A medical scalpel for incising a spherical biological tissue comprising:

a shank; and a planar blade portion integrated with said shank, said planar blade portion comprising:

a first face having a first horizontal plane;

a second face having a second horizontal plane, at least one of said first face and second face being formed flat; and a pointed end;

said planar blade portion having an edge extending continuously in parallel as a whole with said flat first face or said second face from one side portion of said planar blade via said pointed end, said edge defining a virtual flat plane, a partial thickness defined as the distance between the virtual flat plane and the first horizontal plane of said planar blade portion, and a total thickness defined as the distance between the first horizontal plane and the second horizontal plane, wherein said planar blade portion is formed so as to have a ratio of the partial thickness thereof on one side of a virtual flat plane surrounded by said edge to the total thickness thereof within a range from 75 to 93%.

2. The medical scalpel as claimed in claim 1, wherein said edge of the blade portion is formed at an end slope of said first face and an end slope of said second face, and said first face further comprises, along an inner periphery of said end slope, an easy slope having an angle of inclination smaller than that of such end slope.

3. The medical scalpel as claimed in claim 2, wherein said end slope and said easy slope of the first face are abutted to form an arris in parallel with the virtual flat plane surrounded by said edge.

4. The medical scalpel as claimed in claim 2, wherein said end slopes of said first and second faces are finished to have a relatively smooth texture, and said easy slope is finished to have a relatively coarse texture.

5. The medical scalpel as claimed in claim 1 wherein, said blade portion is made of austenitic stainless steel.

6. The medical scalpel as claimed in claim 5, wherein said blade portion is formed by pressing process so as that total thickness of said blade portion has a value not more than 40% of the diameter of the shank.

* * * * *